US010856845B2

(12) United States Patent
Katsube et al.

(10) Patent No.: US 10,856,845 B2
(45) Date of Patent: Dec. 8, 2020

(54) ULTRASOUND PROBE AND ULTRASOUND DIAGNOSIS DEVICE USING THE SAME (71) Applicant: Hitachi, Ltd., Tokyo (JP)

(72) Inventors: Yusaku Katsube, Tokyo (JP); Tatsuo Nakagawa, Tokyo (JP); Yasuyuki Okuma, Tokyo (JP); Yohei Nakamura, Tokyo (JP); Takahide Terada, Tokyo (JP); Shinya Kajiyama, Tokyo (JP); Takuma Nishimoto, Tokyo (JP); Yutaka Igarashi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 498 days.

(21) Appl. No.: 15/763,124

(22) PCT Filed: Oct. 4, 2016

(86) PCT No.: PCT/JP2016/079455
§ 371 (c)(1),
(2) Date: Mar. 26, 2018

(87) PCT Pub. No.: WO2017/061414
PCT Pub. Date: Apr. 13, 2017

(65) Prior Publication Data
US 2018/0192994 A1 Jul. 12, 2018

(30) Foreign Application Priority Data

Oct. 5, 2015 (JP) .................................. 2015-197805

(51) Int. Cl.
*A61B 8/00* (2006.01)
*G01S 7/52* (2006.01)
(Continued)

(52) U.S. Cl.
CPC .......... *A61B 8/4483* (2013.01); *A61B 8/4461* (2013.01); *A61B 8/461* (2013.01);
(Continued)

(58) Field of Classification Search
CPC ..... A61B 8/4483; A61B 8/4461; A61B 8/461; A61B 8/14; G01S 7/5208; G01S 15/8927; B06B 1/0207
See application file for complete search history.

(56) References Cited

U.S. PATENT DOCUMENTS

2008/0027320 A1* 1/2008 Bolorforosh ......... A61B 8/4483
600/439
2008/0238532 A1 10/2008 Hanazawa et al.

FOREIGN PATENT DOCUMENTS

JP 2008-252436 A 10/2008
JP 4557575 B2 10/2010
JP 2011-98072 A 5/2011

OTHER PUBLICATIONS

International Search Report of PCT/JP2016/079455 dated Nov. 29, 2016.

* cited by examiner

Primary Examiner — Peter Luong
(74) Attorney, Agent, or Firm — Mattingly & Malur, PC (57) ABSTRACT An ultrasound diagnosis device includes: an ultrasound probe which transmits an ultrasound wave toward a examinee and receives a reflected wave from the examinee; and a main device which controls the transmitting and receiving of the ultrasound waves from the ultrasound probe and is operated to receive a receiving signal obtained by receiving the reflected wave from the examinee by the ultrasound probe, to generate an ultrasound image of the examinee, and to display the ultrasound image on a display screen, wherein the ultrasound probe includes a plurality of subarrays having a plurality of element circuits transmitting and receiving ultrasound signals and a plurality of reference voltage
(Continued)

sources, and the plurality of subarrays and the plurality of reference voltage sources have a one-to-one correspondence.

14 Claims, 10 Drawing Sheets (51) Int. Cl.
*G01S 15/89* (2006.01)
*B06B 1/02* (2006.01)
*A61B 8/14* (2006.01)

(52) U.S. Cl.
CPC .......... *B06B 1/0207* (2013.01); *G01S 7/5208* (2013.01); *G01S 15/8927* (2013.01); *A61B 8/14* (2013.01)

| | SWITCHING SIGNAL | |
|---|---|---|
| | 0 | 1 |
| SW10 | open | close |
| SW11 | open | close |
| SW12 | close | open |
| SW13 | close | open |

FIG. 7

| UNIT | SWITCHING SIGNAL | |
|---|---|---|
| | 0 | 1 |
| SW20 | open | close |
| SW21 | open | close |
| SW22 | close | open |
| SW23 | close | open |

FIG. 8

| | SWITCHING SIGNAL | |
|---|---|---|
| | 0 | 1 |
| TRANSMISSION /RECEPTION SEPARATION UNIT | open | close |

ULTRASOUND PROBE AND ULTRASOUND DIAGNOSIS DEVICE USING THE SAME

TECHNICAL FIELD

The present invention relates to an ultrasound probe and an ultrasound diagnosis device using the same, and more particularly to, a technique which is effective to solve an interference problem inside an ultrasound probe.

BACKGROUND ART

An ultrasound diagnosis device is a device which is smaller than the other medical image diagnosis devices such as an X-ray diagnosis device or a magnetic resonance imaging (MRI) device and is able to display in real time a state of motion of a examinee such as heart pulsation or fetus movement just by a simple operation of bringing an ultrasound probe into contact with a body surface.

Specifically, the ultrasound diagnosis device transmits ultrasound waves into the examinee by respectively supplying drive signals to a plurality of transducers embedded in the ultrasound probe. Then, the ultrasound diagnosis device receives reflected waves of ultrasound waves caused by a difference in acoustic impedance of biological tissue with the plurality of transducers and generates an ultrasound image based on the reflected waves received by the ultrasound probe.

Here, in the ultrasound diagnosis device, a delay time is controlled for the drive signal supplied to the plurality of transducers and the reflected wave signal obtained from each of the plurality of transducers in order to improve the image quality of the ultrasound image.

Specifically, the ultrasound diagnosis device transmits a beam-formed ultrasound wave to a predetermined focal point of the examinee by controlling the timing of the drive signal to be supplied to each transducer based on the delay time according to a distance between the predetermined focal point in the examinee and each transducer.

Based on the delay time corresponding to the distance between the predetermined focal point in the inside of the examinee and each of the transducers, the transducers receive signals from the predetermined focal point differently in terms of time, and the signals are added as their time is matched, i.e. the signals are phased and added. Thus, the ultrasound diagnosis device generates a line of received signals in focus. As described above, an analog or digital delay circuit is necessary in order to match the signals from a predetermined focal point.

For example, Patent Document 1 discloses a configuration in which an echo signal is stored in a CCD element at a predetermined timing, a delay time is given, and charges of different delay times are output to a common potential well, thereby adding the signals.

CITATION LIST

Patent Document

Patent Document 1: JP 4557575 B2

SUMMARY OF THE INVENTION

Problems to be Solved by the Invention

In order to obtain a three-dimensional image instead of a two-dimensional image, a two-dimensional ultrasound probe that arranges transducers in a two-dimensional array uses several thousand to ten thousand channels of transducers.

In such a two-dimensional ultrasound probe, there is a problem of interference between output signals of different transducers or subarrays each corresponding to a unit of addition processing.

In the two-dimensional ultrasound probe, although the number of cables is reduced with respect to the number of transducers by grouping different transducers and adding processes and outputting signals by the unit of the subarray. However, when the signals are added by using a common reference voltage, signals between different subarrays interfere with each other, and the signals are deteriorated.

Patent Document 1 discloses a method of adding signals by using a common potential well. However, there is no consideration about a problem in which signals between different subarrays interfere with each other through the common potential well, signals between different subarrays interfere with each other, and the signals are deteriorated.

Figure 14:
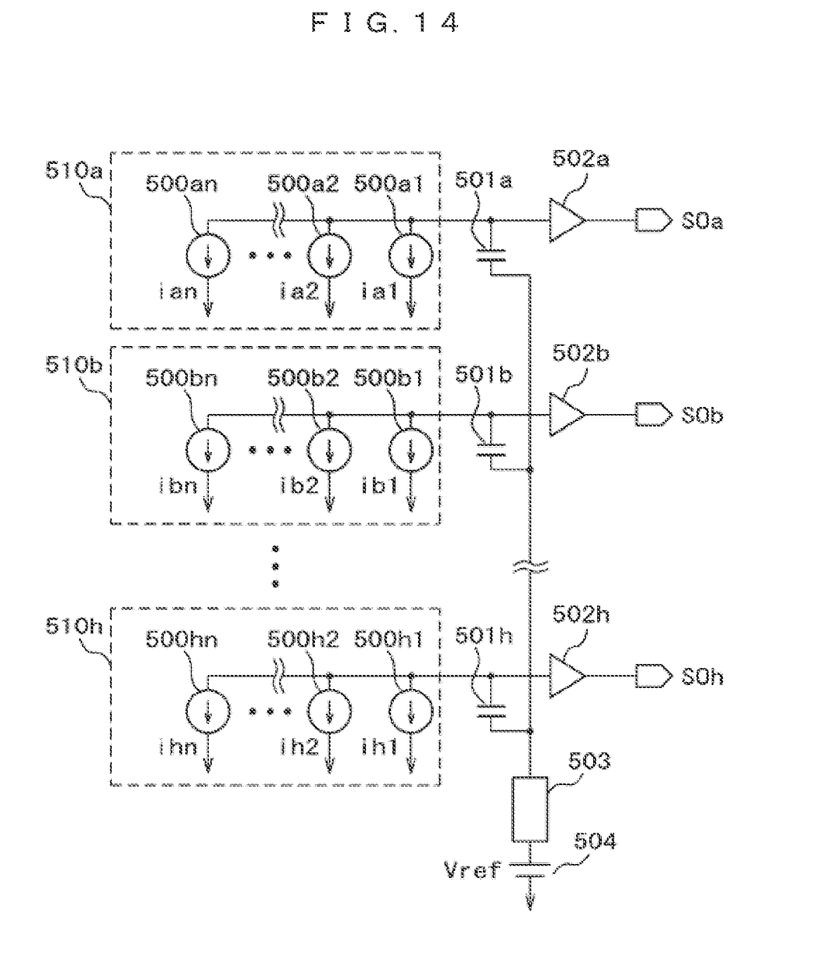
FIG. 14 is an equivalent circuit diagram obtained by modeling an output of a subarray which is a comparative example of the invention.

FIG. 14 illustrates an example of an equivalent circuit of an adding process output unit of a conventional ultrasound probe.

An equivalent circuit of an adding process output unit of a conventional ultrasound probe includes a buffer 502, a electric charge 500 having a different delay time, a subarray 510, an addition capacitance 501, a reference voltage source 504, and a resistor 503.

Hereinafter, a principle of interference between output signals will be described with reference to FIG. 14.

Electric charges 500a1, 500a2, . . . , 500an having different reception delay times inside the subarray 510a respectively output currents ia1, ia2, . . . , ian to the addition capacitance 501a. In the addition capacitance 501a, electric charges having different delay times inside the subarray are added and signals are output to a main device through a buffer 502a. Since the same applies to the subarrays 510b, . . . , 510h, a description thereof will be omitted.

One end of the addition capacitance 501 is connected to the reference voltage source 504 through the resistor 503. The resistor 503 is a model of an output resistance of the reference voltage source 504 and a parasitic resistance of a wiring between the addition capacitance 501 and the reference voltage source 504. The output voltage of the reference voltage source 504 is set within the input voltage range of the buffer 502.

Here, the capacitance value of the addition capacitance 501 is indicated by C, the output voltage of the reference voltage source 504 is indicated by Vref, and the resistance value of the resistor 503 is indicated by R. When the initial electric charge of the addition capacitance 501 is 0 at the time of adding, the input voltage Voa of the buffer 502a is expressed by the following equation.

[Math. 1]

$$Voa = \frac{1}{\omega C}\sum_{K=1}^{n}(iak) + \left(\sum_{m=1}^{n}ibk + \sum_{m=1}^{n}icK + \ldots + \sum_{m=1}^{n}ihk\right)R + Vref \quad (数\ 1)$$

Equation 1

That is, the added output signals of the other subarrays 510b, . . . , 510n shown in the second term are added on the addition result of the subarray 510a of the first term. Similarly, since the output signals from different subarrays are added on the input voltages of other buffers 502, the output signals interfere with each other between outputs of different subarrays.

The interference is reduced by lowering the resistor 503, that is, the parasitic resistance value of the wiring that provides a common potential. For this purpose, a method of increasing the wiring width can be conceived. However, in this method, there is a problem that the wiring area increases and the ultrasound probe becomes large.

An object of the invention is to provide an ultrasound probe capable of obtaining a high-quality image by reducing noise and interference between different subarrays without increasing a wiring area and an ultrasound diagnosis device using the same.

The above and other objects and novel features of the present invention will become apparent from the description of this specification and the accompanying drawings.

Solutions to Problems

A summary of a representative one of the inventions disclosed in the present application will be briefly described as below.

A representative ultrasound probe according to the invention includes a plurality of subarrays having a plurality of element circuits transmitting and receiving ultrasound signals; and a plurality of reference voltage sources, wherein the plurality of subarrays and the plurality of reference voltage sources correspond one-to-one to each other.

Further, another representative ultrasound probe according the invention includes a plurality of subarrays having a plurality of element circuits transmitting and receiving ultrasound signals; a plurality of selector switches corresponding one-to-one to the plurality of subarrays; a plurality of reference voltage sources corresponding one-to-one to the plurality of selector switches; and a control unit controlling the plurality of selector switches.

Further, a representative ultrasound diagnosis device equipped with an ultrasound probe according to the invention includes an ultrasound probe transmitting an ultrasound wave toward a examinee and receiving a reflected wave from the examinee; and a main device controlling the transmitting and receiving of the ultrasound wave from the ultrasound probe and operated to receive a receiving signal obtained by receiving the reflected wave from the examinee by the ultrasound probe, to generate an ultrasound image of the examinee, and to display the ultrasound image on a display screen, in which the ultrasound probe includes a plurality of subarrays having a plurality of element circuits transmitting and receiving ultrasound signals and a plurality of reference voltage sources, and the plurality of subarrays and the plurality of reference voltage sources correspond one-to-one to each other.

Effects of the Invention

According to the invention, the following effects can be obtained.

(1) Interference between signals of an ultrasound probe can be reduced.
(2) An ultrasound probe can be decreased in size.
(3) An ultrasound probe can be decreased in cost by (2).

MODE FOR CARRYING OUT THE INVENTION

The invention provides an ultrasound probe including a plurality of subarrays configured as a plurality of element circuit transmitting and receiving ultrasound signals and a plurality of reference voltage sources and the subarrays and the reference voltage sources are connected one-to-one to each other to prevent interference between output signals of different subarrays.

Further, the invention can obtain a high-quality image by reducing noise and interference between different subarrays without increasing a wiring area by a configuration in which a reference voltage source is provided in each subarray as means for reducing interference between subarrays of an ultrasound probe and a signal is received and transmitted without adding a signal line by switching a wire at the time of receiving and transmitting a signal.

In the following embodiments, for convenience of description, those embodiments will be described as a plurality of sections or embodiments if necessary, but they are not independent from each other unless otherwise stated. Further, one embodiment corresponds to a part or all of modified examples or a detailed or supplementary description of the other embodiment.

In addition, in the following embodiments, when the number of components (including the number, the numerical value, the amount, the range, and the like) are mentioned, those are not limited to a specific number or may be a specific number or more except for a case in which a specific number is particularly stated or a specific number is clearly supposed in principle.

Further, in the following embodiments, it is needless to say that the components (including the element steps and the like) are not essential except for a case in which the components are particularly stated or the components are obviously essential in principle.

Similarly, in the following embodiments, when the shapes, positional relationships, and the like of the components are mentioned, a shape which is substantially similar or similar thereto is included except for a case in which a shape is particularly stated or a shape is not obvious in principle. This also applies to the above-described numerical values and ranges.

In all drawings for describing the embodiments, the same components are denoted by the same reference numerals in principle and a repetitive description thereof will be omitted. Even in a plan view, hatching may be added to easily understand the drawing.

Hereinafter, embodiments will be described in detail.

First Embodiment

Figure 1:
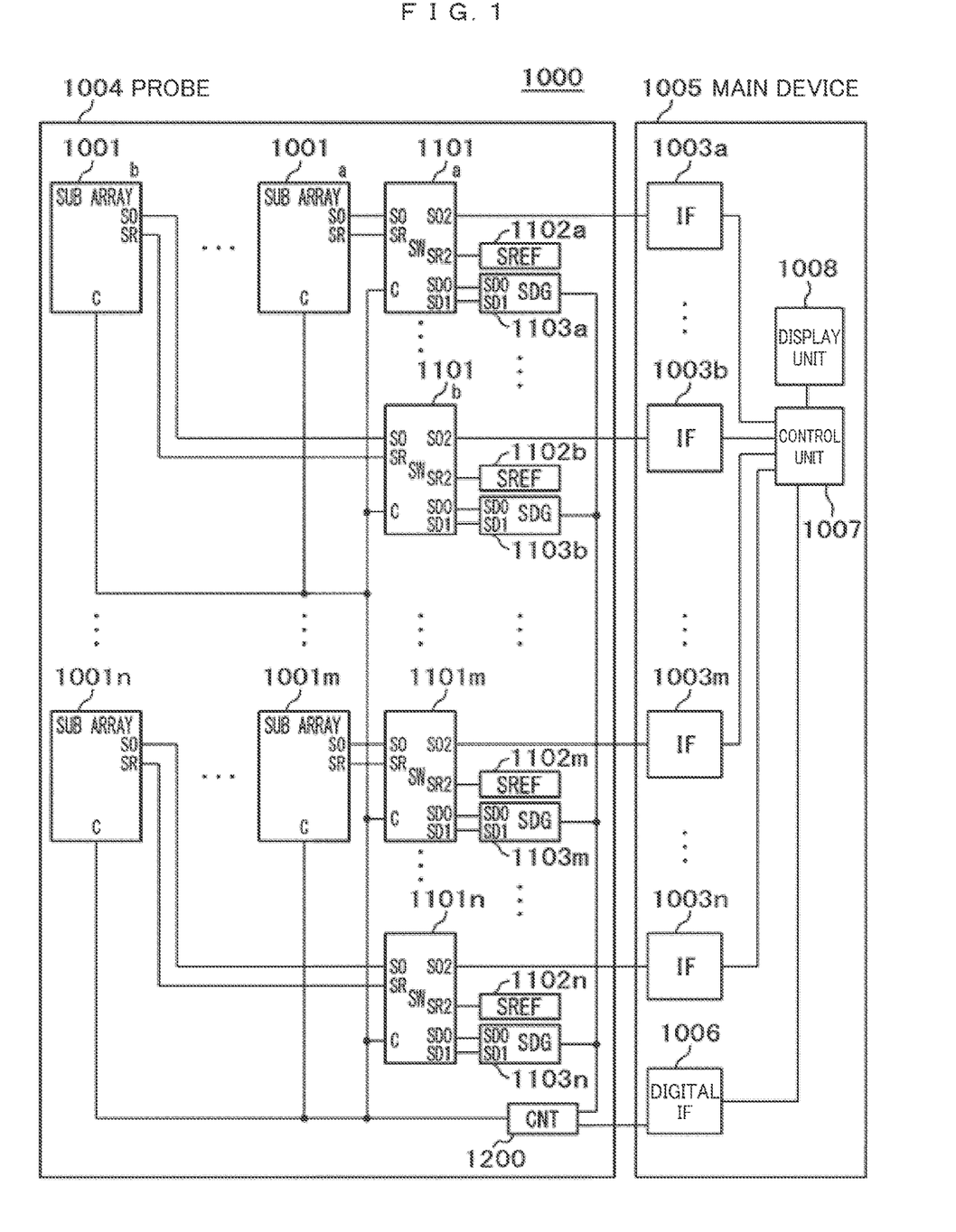
FIG. 1 is a block diagram illustrating a schematic configuration of an ultrasound diagnosis device according to a first embodiment of the invention.

FIG. 1 is a configuration diagram illustrating an example of an ultrasound diagnosis device of a first embodiment.

An ultrasound diagnosis device 1000 includes, as illustrated in FIG. 1, a probe 1004 and a main device 1005.

The probe 1004 includes a plurality of subarrays 1001a, 1001b, and the like, subarray selector switches 1101a, 1101b, and the like, reference voltage sources 1102a, 1102b, and the like, transmission signal sources 1103a, 1103, and the like, and a control circuit (which is indicated by CNT in FIG. 1) 1200.

The main device 1005 includes a plurality of interface circuits (indicated by IF in FIG. 1) 1003a, 1003b, and the like which are connected to the subarray selector switches 1101a, 1101b, and the like of the probe 1004, a digital interface (indicated by a digital IF in FIG. 1) 1006 which is connected to the control circuit (CNT) 1200 of the probe 1004, a control unit 1007 which is connected to the interface circuits 1003a, 1003b, and the like, and a display unit 1008 which displays an ultrasound image while being connected to the control unit 1007.

Each of the subarray selector switch 1101, the reference voltage source (SREF) 1102, and the transmission signal source (SDG) 1103 of the probe 1004 and each interface circuit 1003 of the main device 1005 are provided in each subarray 1001. In the following description, the suffixes a, b, c, and the like indicate the same components and are omitted unless particularly necessary.

Figure 2:
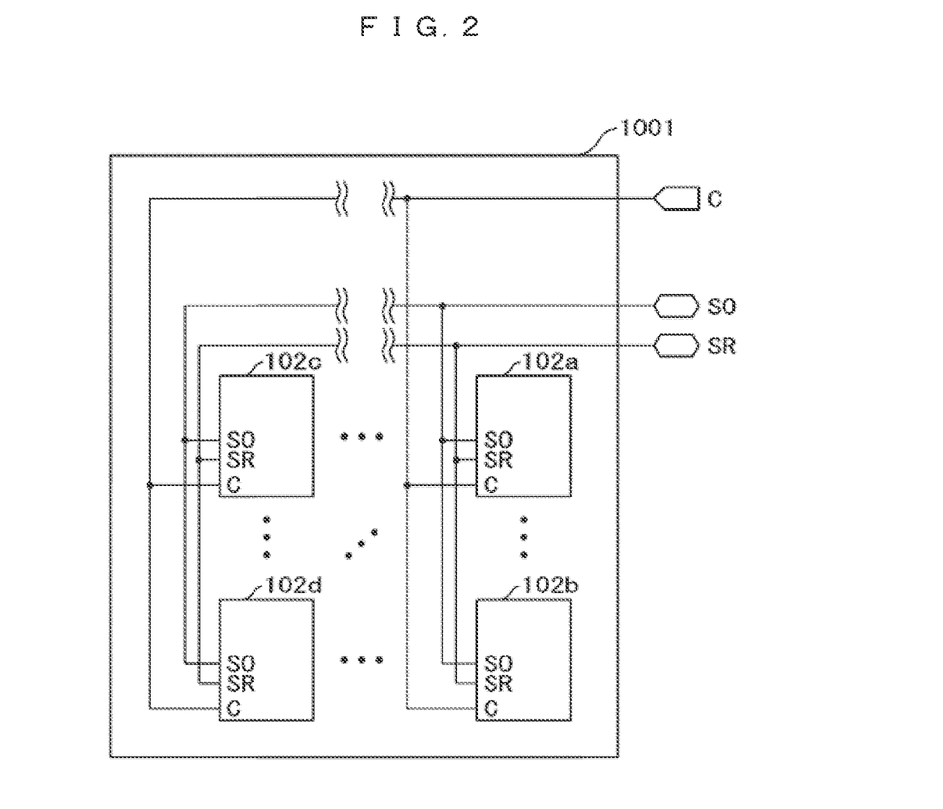
FIG. 2 is a block diagram illustrating a configuration of one subarray of an ultrasound probe of the ultrasound diagnosis device of the first embodiment of the invention.

FIG. 2 is a block diagram illustrating an example of a configuration of one subarray 1001 of the probe 1004.

Each subarray 1001 includes a plurality of single element circuits 102a, 102b, and the like. For example, 128 subarrays 1001 are provided inside the probe 1004. The single element circuit 102 has a configuration in which 64 elements are arranged in a matrix of approximately 8 by 8 in each subarray 1001.

Figure 3:
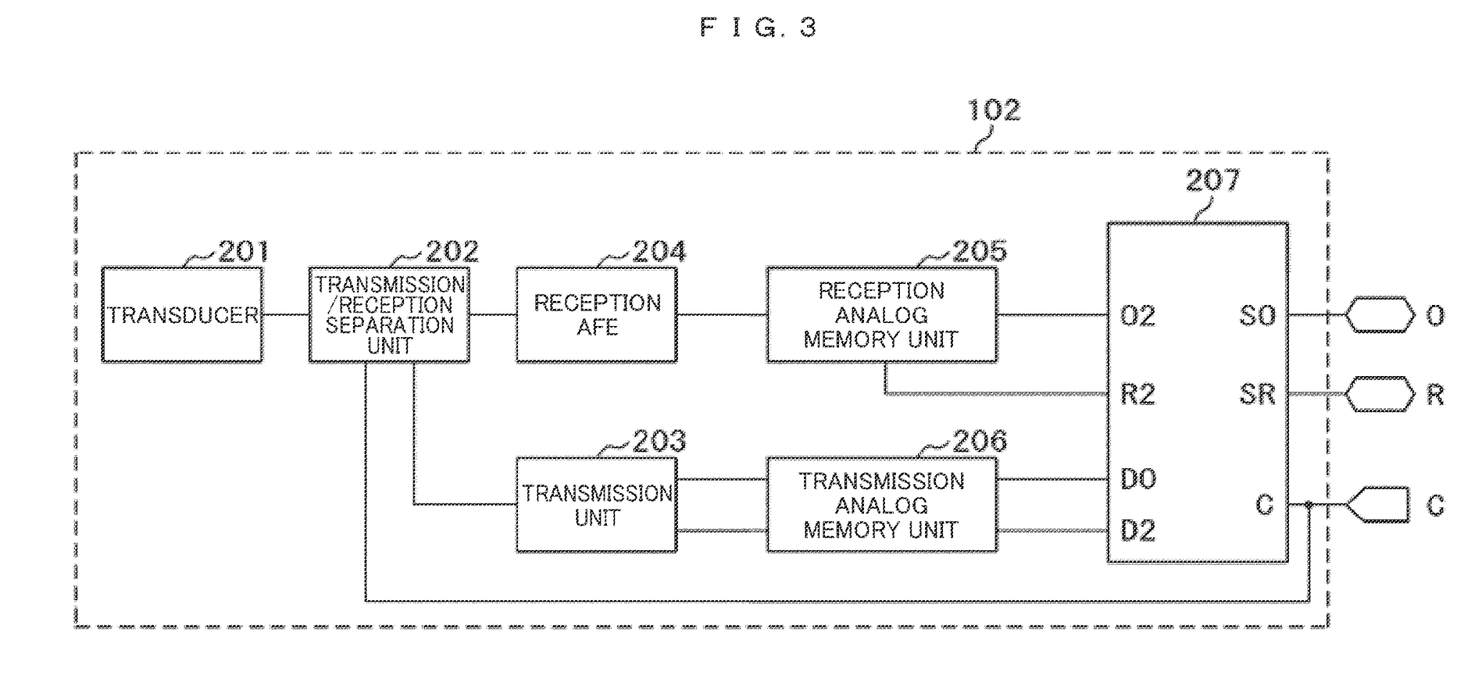
FIG. 3 is a block diagram illustrating a configuration of a single element circuit of the ultrasound probe of the ultrasound diagnosis device of the first embodiment of the invention.

FIG. 3 is a block diagram illustrating an example of a configuration of the single element circuit 102 of the subarray 1001.

As illustrated in the drawings, the single element circuit 102 which is a transmission/reception unit includes a transducer 201, a transmission/reception separation unit 202, a reception analog front end portion (indicated by a reception AFE in FIG. 2) 204, a reception analog memory unit 205 delaying a reception, a transmission unit 203, a transmission analog memory unit 206 delaying a transmission, and an element circuit selector switch 207.

Figure 4:
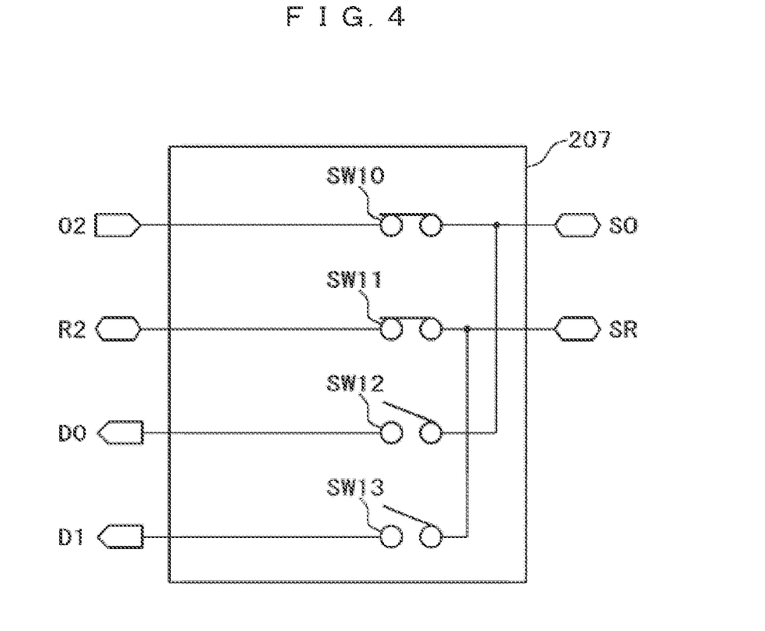
FIG. 4 is a circuit block diagram illustrating a configuration of an element circuit selector switch of the ultrasound probe of the ultrasound diagnosis device of the first embodiment of the invention.

FIG. 4 is a block diagram illustrating an example of a configuration of the element circuit selector switch 207 of the single element circuit 102.

The element circuit selector switch 207 includes switches SW10, SW11, SW12, and SW13.

The switch SW10 is inserted between a terminal O2 and a terminal SO.

The switch SW11 is inserted between a terminal R2 and a terminal SR.

The switch SW12 is inserted between a terminal D0 and the terminal SO.

The switch SW13 is inserted between a terminal D1 and the terminal SR.

Figure 5:
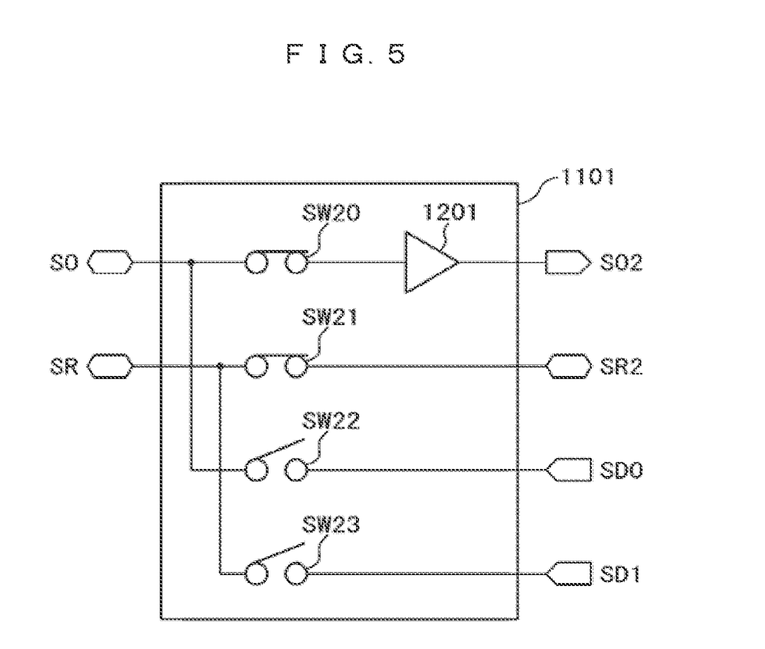
FIG. 5 is a circuit block diagram illustrating a configuration of a subarray selector switch of the ultrasound probe of the ultrasound diagnosis device of the first embodiment of the invention.

FIG. 5 is a block diagram illustrating an example of a configuration of the subarray selector switch 1101.

The subarray selector switch 1101 includes switches SW20, SW21, SW22, and SW23 and a buffer 1201.

The switch SW20 is inserted between the buffer 1201 and the terminal SO. The switch SW21 is inserted between a terminal SR2 and the terminal SR.

The switch SW22 is inserted between a terminal SD0 and the terminal SO.

The switch SW23 is inserted between a terminal SD1 and the terminal SR.

The buffer 1201 is inserted between the switch SW20 and a terminal SO2.

The terminal SO and the terminal SR of the subarray selector switch 1101 are respectively and commonly connected to all of the single element circuits 102 of the subarray 1001 and are respectively connected to the terminal SO and the terminal SR of the element circuit selector switch 207 of the single element circuit 102.

The terminal SO2 of the subarray selector switch 1101 is connected to the interface circuit 1003 of the main device 1005, the terminal SR2 is connected to the reference voltage source 1102, and the terminal SD0 and the terminal SD1 are respectively connected to the transmission signal source 1103.

The terminal O2 and the terminal R2 of the element circuit selector switch 207 are respectively connected to the reception analog memory unit 205 and the terminal D0 and the terminal D1 are respectively connected to the transmission analog memory unit 206.

Figure 10:
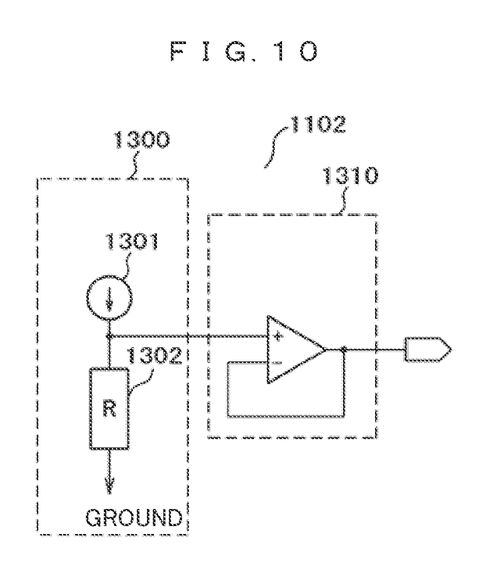
FIG. 10 is a circuit block diagram illustrating a configuration of a reference voltage source of the first embodiment of the invention.

FIG. 10 is a block diagram illustrating an example of a configuration of the reference voltage source 1102.

The reference voltage source 1102 includes a reference voltage setting circuit 1300 and a buffer circuit 1310. The reference voltage setting circuit 1300 includes a current source 1301 and a resistor 1302. The buffer circuit 1310 constitutes a voltage follower.

In the reference voltage setting circuit 1300, one end of the resistor 1302 is connected to the current source 1301 and the other end thereof is connected to a ground potential. When the current value of the current source 1301 is indicated by I and the resistance value of the resistor 1302 is indicated by R, a reference voltage of IR is output from the reference voltage setting circuit 1300 and is input to the buffer circuit 1310. The buffer circuit 1310 constitutes a voltage follower and outputs the input reference voltage with low-output impedance.

Hereinafter, an ultrasound signal transmitting and receiving operation performed in the transducer 201 will be described with reference to FIGS. 1, 2, and 3.

A transmission input signal SD1 output from the transmission signal source 1103 of FIG. 1 is output from the terminal SR and is input to the terminal SR of the element circuit selector switch 207 while the switch SW23 of the subarray selector switch 1101 of FIG. 1 is turned on and the switch SW21 thereof is turned off by the switching signal C output from the control circuit (CNT) 1200 of the probe 1004 controlled by the control unit 1007 through the digital IF 1006 of the main device 1005, so that the signal is commonly input to the single element circuit 102 inside the subarray 1001.

The transmission input signal input to the single element circuit 102 is output from the terminal D1 and is input to the transmission analog memory unit 206 of FIG. 3 while the switch SW11 of the element circuit selector switch 207 of FIG. 3 is turned off and the switch SW13 thereof is turned on by the switching signal C from the control circuit 1200.

The transmission input signal SD0 output from the transmission signal source 1103 of FIG. 1 is output from the terminal SO and is input to the terminal SO of the element circuit selector switch 207 while the switch SW22 of the subarray selector switch 1101 of FIG. 1 is turned on and the switch SW20 thereof is turned off by the switching signal C from the control circuit (CNT) 1200 of the probe 1004 controlled by the control unit 1007 through the digital IF 1006 of the main device 1005, so that the signal is commonly input to the single element circuit 102 inside the subarray 1001.

The transmission input signal input to the single element circuit 102 is output from the terminal D0 and is input to the transmission analog memory unit 206 of FIG. 3 while the switch SW10 of the element circuit selector switch 207 of FIG. 3 is turned off and the switch SW12 thereof is turned on by the switching signal C of the control circuit 1200.

Although not illustrated in the drawings, in the transmission analog memory unit 206, the transmission input signal is sampled and stored in a memory based on a control signal from a digital circuit outputting a control signal for delay control and is output to the transmission unit 203 after a certain delay time (a time corresponding to a distance from a probe at a portion to which an ultrasound wave needs to be transmitted). The transmission unit 203 converts a level to a high-voltage signal having a positive or negative amplitude according to the values of the input transmission input signals D0 and D1 and drives the transducer 201 through the transmission/reception separation unit 202. The ultrasound signal is output from the transducer 201. Further, the ultrasound signal output from the transducer 201 and reflected by the examinee is received by the transducer 201.

The ultrasound signal received by the transducer 201 is separated by the transmission/reception separation unit 202 and is input to the reception analog front end portion 204. In the reception analog front end portion 204, a received signal is amplified and filtered.

The signal output from the reception analog front end portion 204 is input to the reception analog memory unit 205. Although not illustrated in the drawings, the reception analog memory unit 205 samples and stores the analog input signal in a memory based on a control signal from a digital circuit outputting a control signal for delay control and outputs the analog signal after a certain delay time.

Regarding the amplitude of the signal input to the reception analog memory unit 205, a reference voltage of an output signal without amplitude is output from the reference voltage source 1102 of FIG. 1 and is input to the terminal SR2 of the subarray selector switch 1101. By the switching signal C from the control circuit 1200, the subarray selector switch 1101 is switched so that the switch SW21 is turned on and the switch SW23 is turned off. Accordingly, the reference voltage is output from the output terminal SR of the subarray selector switch 1101 and is input to the input terminal SR of the element circuit selector switch 207 of the single element circuit 102 inside the subarray 1001. When the switch SW11 of the element circuit selector switch 207 is turned on and the switch SW13 thereof is turned off by the switching signal C from the control circuit 1200, the reference voltage is input from the terminal R2 of the element circuit selector switch 207 to the reception analog memory unit 205.

A signal output from the reception analog memory unit 205 to which the reference voltage is input is input to the terminal O2 of the element circuit selector switch 207. Then, when the switch SW10 of the element circuit selector switch 207 is turned on and the switch SW12 thereof is turned off by the switching signal C from the control circuit 1200, the signal is output from the terminal SO of the element circuit selector switch 207, that is, the single element circuit 102. By the connection to a common signal line (a line connected to SO in FIG. 2) by the unit of the subarray, the output signal from the terminal SO of the single element circuit 102 in the subarray 1001 is added by the unit of the subarray.

A signal obtained by adding the output signals from all single element circuits 102 inside the subarray 1001 is input from the terminal SO of the subarray 1001 to the terminal SO of the subarray selector switch 1101.

When the switch SW20 of the subarray selector switch 1101 is turned on and the switch SW22 thereof is turned off by the switching signal C output from the control circuit 1200, the signal is output from the terminal SO2 of the subarray selector switch 1101 and is transmitted to the interface circuit 1003 of the main device 1005.

The signal transmitted to the interface circuit 1003 is transmitted to the control unit 1007 and the signals respectively corresponding to the subarrays 1001 are integrated by the control unit 1007 so that an ultrasound image of the examinee is formed. This formed ultrasound image is transmitted to the display unit 1008 and is displayed on the display screen of the display unit.

Figure 6:
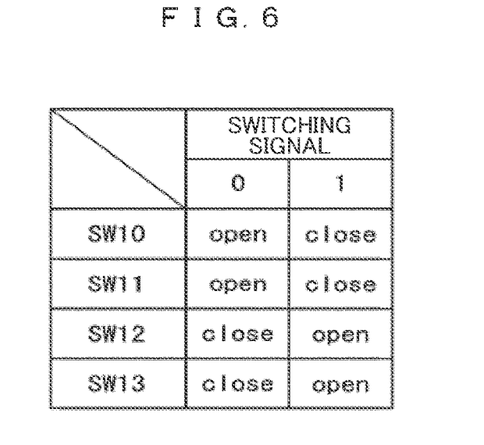
FIG. 6 is a truth table showing a control example of the element circuit selector switch of the ultrasound probe of the ultrasound diagnosis device of the first embodiment of the invention.

FIG. 6 is a truth table showing a control example of the element circuit selector switch 207 of the single element circuit 102.

Figure 7:
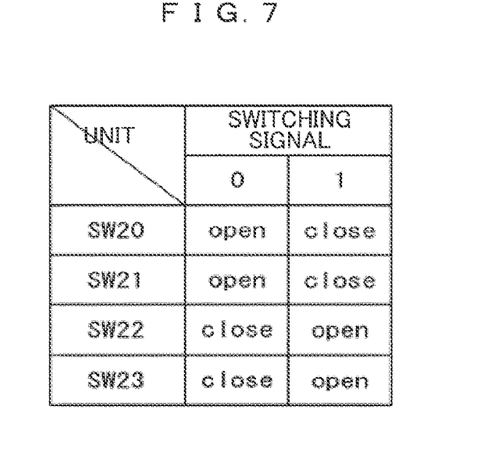
FIG. 7 is a truth table showing a control example of the subarray selector switch of the ultrasound probe of the ultrasound diagnosis device of the first embodiment of the invention.

FIG. 7 is a truth table showing a control example of the subarray selector switch 1101.

Figure 8:
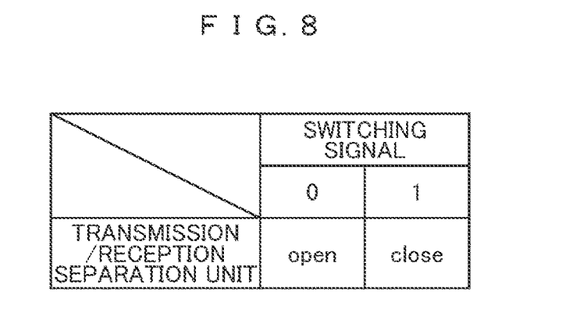
FIG. 8 is a truth table showing a control example of a transmission/reception separation unit of the ultrasound probe of the ultrasound diagnosis device of the first embodiment of the invention.

FIG. 8 is a truth table showing a control example of the transmission/reception separation unit 202.

The switches SW10, SW11, SW12, and SW13 of the element circuit selector switch 207 of the single element circuit 102, the switches SW20, SW21, SW22, and SW23 of the subarray selector switch 1101, and the transmission/reception separation unit 202 are set to a mode of CLOSE indicating a state in which the terminals of the switch are connected and the switch is turned on or a mode of OPEN indicating a state in which the terminals of the switch are not connected to each other and the switch is turned off in response to the digital value of 0 or 1 of the switching signal C output from the control circuit 1200. The switching signal C output from the control circuit 1200 is controlled by the control unit 1007 through the digital IF 1006 of the main device.

Figure 9:
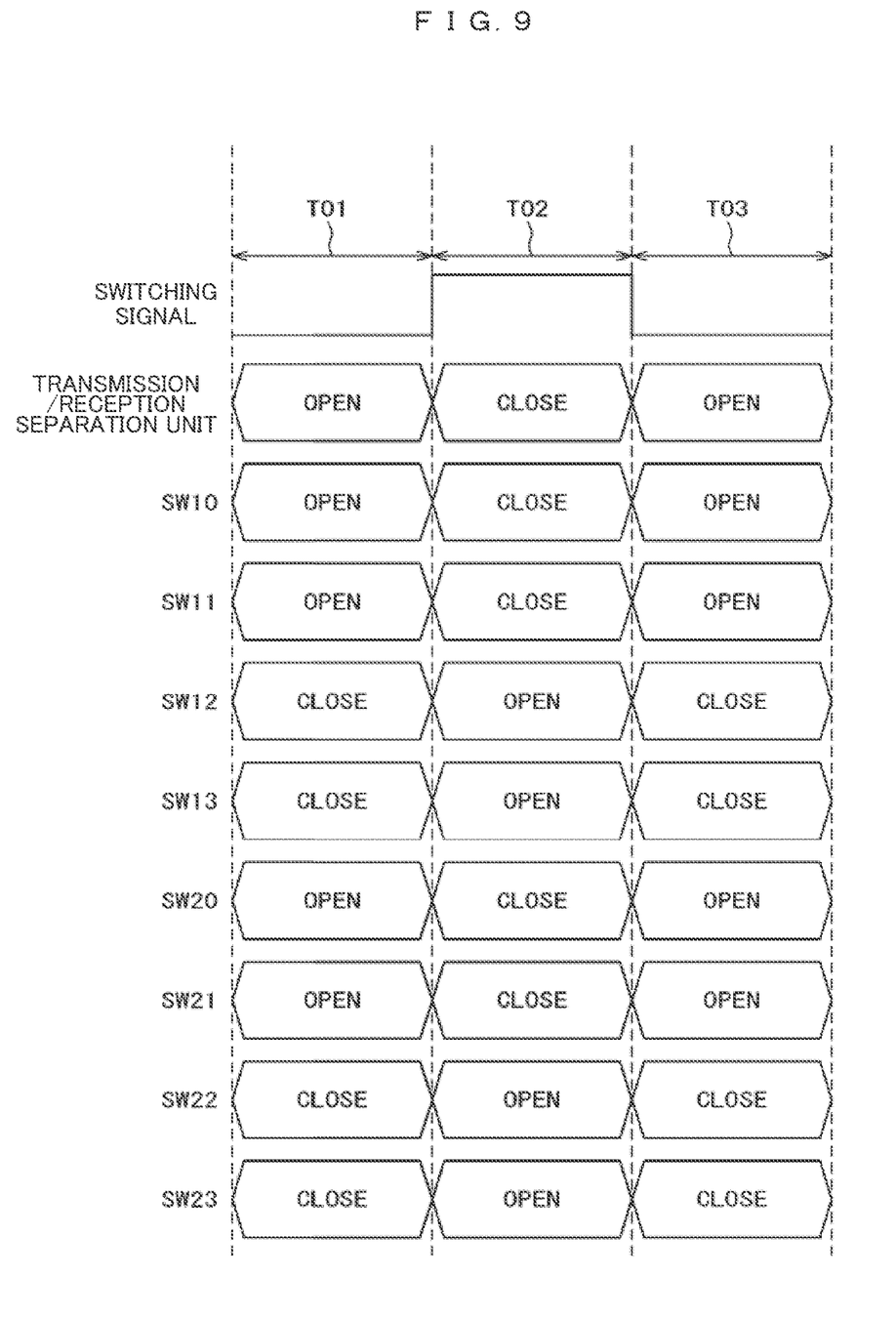
FIG. 9 is a timing chart showing control timing examples of the element circuit selector switch and the subarray selector switch of the ultrasound probe of the ultrasound diagnosis device of the first embodiment of the invention.

FIG. 9 is a timing chart showing control timing examples of the transmission/reception separation unit 202 and the element circuit selector switch 207 of the single element circuit 102 and the subarray selector switch 1101.

Hereinafter, the control timings of the element circuit selector switch 207, the subarray selector switch 1101, and the transmission/reception separation unit 202 will be described with reference to FIGS. 6 to 9.

In FIG. 9, the switching signal C is set to 0 during a period of T01. The transmission/reception separation unit 202 is set to OPEN so that the reception analog front end portion 204 is separated from the transmission unit 203 and the transducer 201. The switches SW10 and SW11 of the element circuit selector switch 207 and the switches SW20 and SW21 of the subarray selector switch 1101 are set to OPEN and the switches SW12 and SW13 of the element circuit selector switch 207 and SW22 and SW23 of the subarray selector switch 1101 are set to CLOSE.

Thus, based on the control signals output to the transmission signal sources 1103 from the control circuit 1200 of the probe 1004 controlled by the control unit 1007 through the digital IF 1006 of the main device 1005, the transmission input signal output from the transmission signal source 1103 can pass through the switches SW12, SW13, SW22, and SW23 and can be input to the transmission analog memory unit 206. That is, the ultrasound signal can be output from the transducer 201.

The switching signal C is set to 1 during a period of T02 in FIG. 9. The transmission/reception separation unit 202 is set to CLOSE so that the reception analog front end portion 204 is connected to the transducer 201. The switches SW10, SW11, SW20, and SW21 are set to CLOSE and the switches SW12, SW13, SW22, and SW23 are set to OPEN. Thus, the reference voltage output from the reference voltage source 1102 can pass through the switches SW11 and SW21 and can be input to the reception analog memory unit 205. The signal output from the reception analog memory unit 205 passes through the switch SW10. Then, the output signal of the single element circuit 102 inside the subarray 1001 is added by the unit of the subarray, passes through the switch SW20, is input to the buffer 1201, and is output to the main device 1005. That is, the ultrasound signal received by the transducer 201 can be received by the main device 1005.

As described above, since the reference voltage source is provided for each subarray 1001, no interference occurs between the output signals of the plurality of subarrays 1001. Meanwhile, it is necessary to provide a wiring for outputting the reference voltage in each subarray 1001. However, as illustrated in FIG. 5, when the reference voltage is input from the terminal SR2 to the subarray selector switch 1101, the transmission signal is input from the terminal SD1 thereto, and the switches SE21 and SW23 are switched, any one of the reference voltage and the transmission signal is output from the terminal SR of the subarray selector switch 1101 to be shared with the wiring SR input to the subarray 1001. Accordingly, it is possible to provide an ultrasound probe capable of preventing interference between output signals of the subarrays 1001 while suppressing a wiring area.

Figure 11:
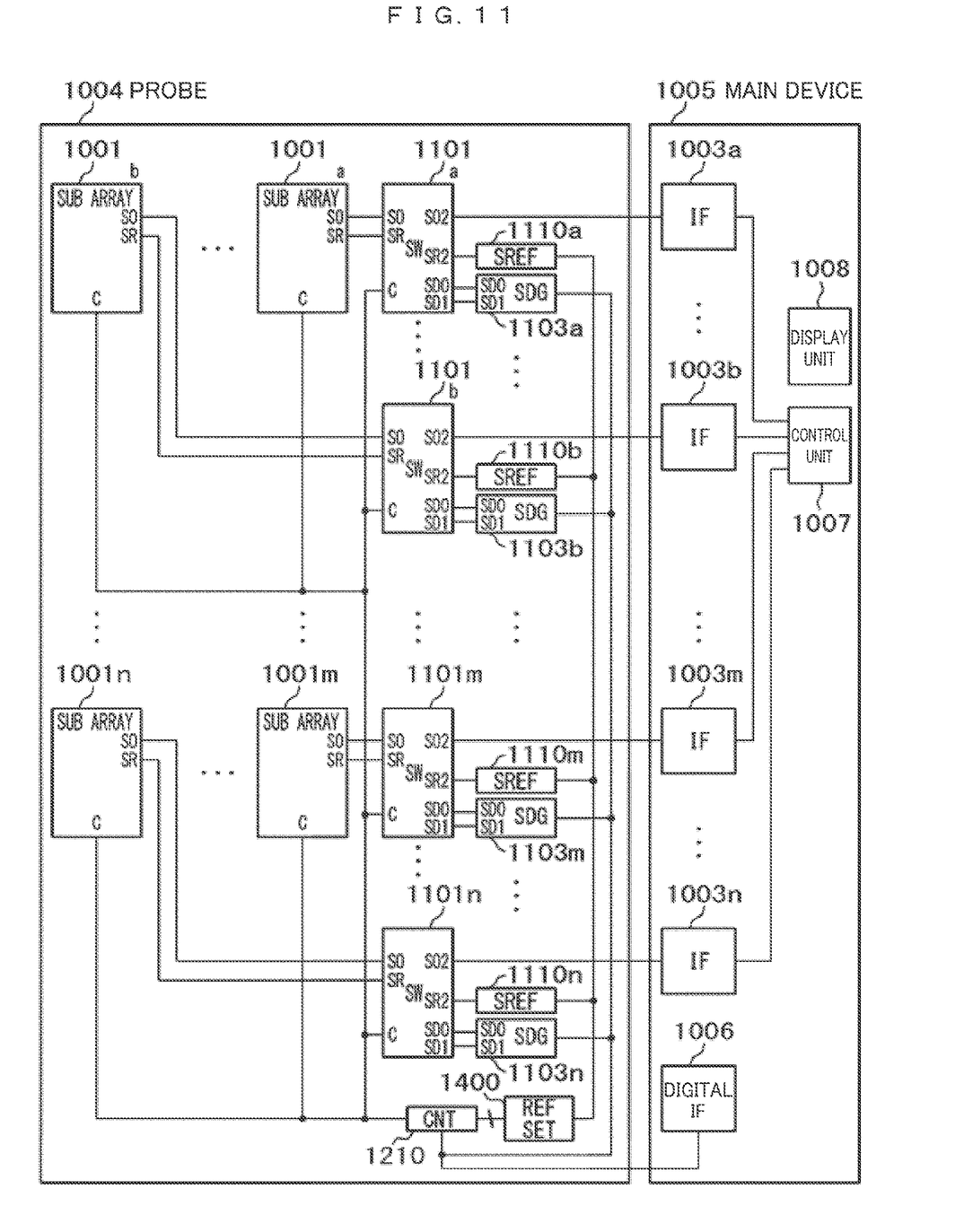
FIG. 11 is a block diagram illustrating a schematic configuration of an ultrasound diagnosis device of a second embodiment of the invention.

Further, in this embodiment, the buffer circuit 1310 of FIG. 11 is not limited to the voltage follower and any configuration capable of realizing low-output impedance may be used. For example, an emitter follower, a source follower, and a non-inverting amplifier using an operational amplifier can be considered.

Further, in FIG. 3, the reception analog memory unit 205 and the transmission analog memory unit 206 may be used for both transmission and reception. Also in this case, when the element circuit selector switch 207 is connected to the transmission input terminal D0, the terminal D1, the reception output terminal O, and the reference voltage input terminal R, the wiring of the reference voltage and the wiring of the transmission input signal can be shared.

Second Embodiment

Figure 12:
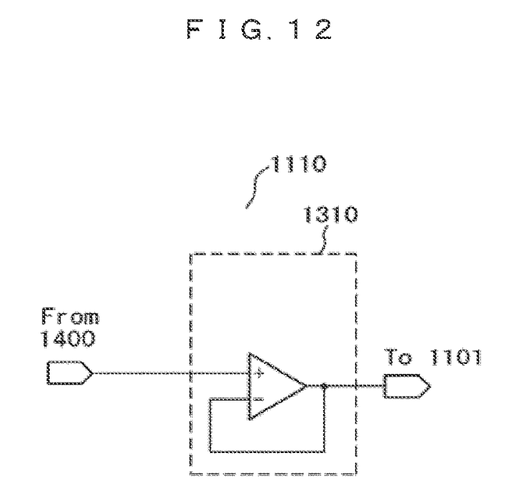
FIG. 12 is a circuit block diagram illustrating a configuration of a reference voltage source of the second embodiment of the invention.
Figure 13:
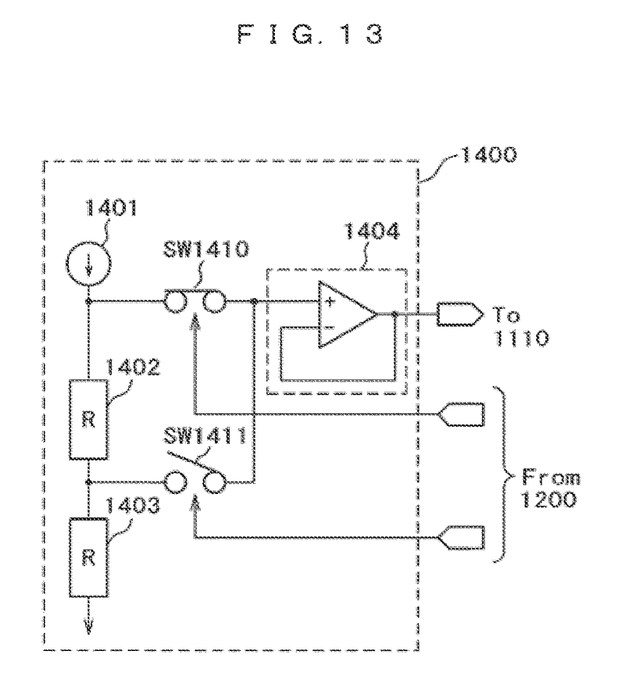
FIG. 13 is a circuit block diagram illustrating a configuration of a reference voltage setting circuit of the second embodiment of the invention.

FIG. 11 is a diagram in which the reference voltage setting circuit 1300 inside the reference voltage source 1102 illustrated in FIG. 10 is replaced by a reference voltage setting circuit 1400 illustrated in FIG. 13 and is shared with the reference voltage sources compared to FIG. 1. Hereinafter, a second embodiment of the invention will be described with reference to FIGS. 11 to 13.

The reference voltage signal output from the reference voltage setting circuit 1400 is connected to the subarray selector switch 1101 through the reference voltage source 1110. The reference voltage setting circuit 1400 sets the reference voltage based on the control signal input from the control circuit 1210 and outputs the voltage to the reference voltage source 1110. The reference voltage source 1110 serves as a buffer and is operated to receive an output of the reference voltage setting circuit and output the voltage with low-output impedance. Since the other operations are the same as those of the first embodiment of the invention, a description thereof will be omitted.

FIG. 12 illustrates an example of the reference voltage source 1110 of this embodiment. FIG. 13 illustrates an example of the reference voltage setting circuit 1400 of this embodiment.

The reference voltage source 1110 is configured as the buffer circuit 1310 and the buffer circuit 1310 constitutes a voltage follower and outputs the input reference voltage with low-output impedance.

The reference voltage setting circuit 1400 illustrated in FIG. 13 includes a current source 1401, a resistor 1402, a resistor 1403, switches SW1419 and SW1411, and a buffer circuit 1404.

The current source 1401 allows a current to flow to the resistors 1402 and 1403 connected in series to each other and one end of the resistor 1403 is connected to a ground potential. When the current value of the current source 1401 is indicated by I and the resistance values of the resistor 1402 and the resistor 1403 are indicated by R, the reference voltages of I2R and IR are respectively applied to one ends of the switch SW1400 and the switch SW1401.

The switch SW1410 and the switch SW1411 are controlled by the control circuit 1200. Then, when the switch SW1410 is closed and the switch SW1411 is opened, the reference voltage of I2R is input to the buffer circuit 1404. Meanwhile, when the switch SW1410 is opened and the switch SW1411 is closed, the reference voltage of IR is input to the buffer circuit 1404. The buffer circuit 1404 constitutes a voltage follower and outputs the input reference voltage with low-output impedance.

That is, since the buffer circuit unit 1310 with a low-output impedance output is connected one-to-one to each subarray in order to supply the reference voltage to the subarray 1001, it is possible to reduce interference between different subarrays.

Meanwhile, the reference voltage setting circuit 1400 for setting the reference voltage is shared with the reference voltage sources 1110 as illustrated in FIG. 12. For that reason, it is possible to reduce an area and power consumption compared to a method in which the reference voltage setting circuit 1400 is provided inside each reference voltage source.

Further, when the switches SE1410 and SE1411 of the reference voltage setting circuit 1400 are controlled by the signal from the control circuit 1210, the reference voltage can be switched. For example, when it is assumed that the reception AFE 204 or the reception analog memory unit 205 illustrated in FIG. 3 is operated in various modes consuming different power, the reference voltage can be switched in synchronization with the mode.

Further, the buffer circuit 1310 and the buffer circuit 1404 of FIGS. 13 and 14 of this embodiment are not limited to the voltage followers and any configuration capable of realizing low-output impedance may be employed. For example, an emitter follower, a source follower, and a non-inverting amplifier using an operational amplifier can be considered. Further, a configuration without the buffer circuit 1404 of FIG. 14 may be employed. If there is concern of the influence of interference due to coupling when the peripheral wiring is close to the wiring between the reference voltage setting circuit 1400 and the reference voltage source 1110, the buffer circuit 1404 can be used. In this case, since the output of the buffer circuit 1404 has low-output impedance, the influence of interference is reduced.

While the invention contrived by the present inventor has been described in detail based on the embodiments above, it is needless to say that the invention is not limited to the above-described embodiments and various modifications can be made within a scope not departing from the gist thereof.

In addition, the invention is not limited to the above-described embodiments and includes various modified examples. For example, the above-described embodiments are described in detail in order to easily describe the invention and are not limited to essentially include all configurations described above.

Further, a part of the configuration of one embodiment can be replaced with the configuration of another embodiment and the configuration of another embodiment can be added to the configuration of one embodiment. Further, it is possible to add, delete, and replace other configurations with respect to a part of the configurations of each embodiment.

REFERENCE SIGNS LIST

1004: probe, 1001: subarray, 102: single element circuit, 1201: buffer, 1200: control circuit, 1005: main device, 1003: interface circuit, 201: transducer, 202: transmission/reception separation unit, 203: transmission unit, 204: reception analog front end portion, 205: reception analog memory unit, 206: transmission analog memory unit, 207: element circuit selector switch, 1101: subarray selector switch, 1102: reference voltage source, 1103: transmission signal source, SW10, SW11, SW12, SW13: switch, SW20, SW21, SW22, SW23: switch

The invention claimed is:

1. An ultrasound probe comprising:
a plurality of subarrays having a plurality of element circuits transmitting and receiving ultrasound signals; and
a plurality of reference voltage sources,
wherein the plurality of subarrays and the plurality of reference voltage sources correspond one-to-one to each other.

2. The ultrasound probe according to claim 1,
wherein the plurality of subarrays and reference voltage sources corresponding one-to-one to each other are connected through selector switches respectively corresponding one-to-one to the plurality of subarrays and the plurality of reference voltage sources.

3. The ultrasound probe according to claim 2, further comprising:
a plurality of transmission signal sources corresponding one-to-one to the plurality of subarrays,
wherein the plurality of subarrays and transmission signal sources corresponding one-to-one to each other are connected through the selector switches.

4. The ultrasound probe according to claim 1, further comprising:
a reference voltage setting circuit,
wherein the reference voltage source is configured as a buffer circuit and is connected to the reference voltage setting circuit and the reference voltage source buffers an output signal of the reference voltage setting circuit with a low-output impedance.

5. An ultrasound probe comprising:
a plurality of subarrays having a plurality of element circuits transmitting and receiving ultrasound signals;
a plurality of selector switches corresponding one-to-one to the plurality of subarrays;
a plurality of reference voltage sources corresponding one-to-one to the plurality of selector switches; and
a control unit controlling the plurality of selector switches.

6. The ultrasound probe according to claim 5, further comprising:
a plurality of transmission signal sources corresponding one-to-one to the plurality of subarrays,
wherein the control unit controls the plurality of selector switches to turn on or off a circuit connecting the plurality of reference voltage sources respectively corresponding one-to-one to the plurality of subarrays and to turn on or off a circuit connecting the transmission signal sources respectively corresponding one-to-one to the plurality of subarrays.

7. The ultrasound probe according to claim 6,
wherein the control unit switches an on/off state of a circuit connecting the plurality of reference voltage sources respectively corresponding one-to-one to the plurality of subarrays and switches an on/off state of a circuit connecting the transmission signal sources respectively corresponding one-to-one to the plurality of subarrays at opposite timings.

8. An ultrasound diagnosis device equipped with an ultrasound probe comprising:
an ultrasound probe transmitting an ultrasound wave toward a examinee and receiving a reflected wave from the examinee; and
a main device controlling the transmitting and receiving of the ultrasound wave from the ultrasound probe and operated to receive a receiving signal obtained by receiving the reflected wave from the examinee by the ultrasound probe, to generate an ultrasound image of the examinee, and to display the ultrasound image on a display screen,
wherein the ultrasound probe includes a plurality of subarrays having a plurality of element circuits transmitting and receiving ultrasound signals and a plurality of reference voltage sources, and wherein the plurality of subarrays and the plurality of reference voltage sources correspond one-to-one to each other.

9. The ultrasound diagnosis device equipped with the ultrasound probe according to claim 8, wherein the plurality of subarrays and reference voltage sources corresponding one-to-one to each other of the ultrasound probe are connected through selector switches respectively corresponding one-to-one to the plurality of subarrays and reference voltage sources.

10. The ultrasound diagnosis device equipped with the ultrasound probe according to claim 9, wherein the ultrasound probe further includes a plurality of transmission signal sources corresponding one-to-one to the plurality of subarrays, and wherein the plurality of subarrays and transmission signal sources corresponding one-to-one to each other are connected through the selector switches.

11. The ultrasound diagnosis device equipped with the ultrasound probe according to claim 10, wherein the ultrasound probe includes a plurality of selector switches corresponding one-to-one to the plurality of subarrays and a control unit controlling the plurality of selector switches, and wherein the plurality of reference voltage sources correspond one-to-one to the plurality of selector switches.

12. The ultrasound diagnosis device equipped with the ultrasound probe according to claim 11, wherein the control unit of the ultrasound probe switches an on/off state of the selector switch connecting the plurality of reference voltage sources respectively corresponding one-to-one to the plurality of subarrays and switches an on/off state of the selector switch connecting the plurality of transmission signal sources respectively corresponding one-to-one to the plurality of subarrays.

13. The ultrasound diagnosis device equipped with the ultrasound probe according to claim 11, wherein the control unit of the ultrasound probe switches an on/off state of the selector switch connecting the plurality of reference voltage sources respectively corresponding one-to-one to the plurality of subarrays and switches an on/off state of the selector switch connecting the plurality of transmission signal sources respectively corresponding one-to-one to the plurality of subarrays at opposite timings.

14. The ultrasound diagnosis device equipped with the ultrasound probe according to claim 8, wherein the ultrasound probe further includes a reference voltage setting circuit, wherein the plurality of reference voltage sources are configured as buffer circuits and are connected to the reference voltage setting circuit, and wherein the plurality of reference voltage sources buffer an output signal of the reference voltage setting circuit with a low-output impedance.

* * * * *